United States Patent
Jin et al.

(10) Patent No.: US 9,220,469 B2
(45) Date of Patent: Dec. 29, 2015

(54) SYSTEMS AND METHODS FOR CORRECTING DETECTOR ERRORS IN COMPUTED TOMOGRAPHY IMAGING

(71) Applicant: General Electric Company, Schenectady, NY (US)

(72) Inventors: Yannan Jin, Schenectady, NY (US); Peter Michael Edic, Albany, NY (US); Vladimir A. Lobastov, Clifton Park, NY (US); Hewei Gao, Waukesha, WI (US); Geng Fu, Clifton Park, NY (US)

(73) Assignee: GENERAL ELECTRIC COMPANY, Niskayuna, NY (US)

( * ) Notice: Subject to any disclaimer, the term of this patent is extended or adjusted under 35 U.S.C. 154(b) by 174 days.

(21) Appl. No.: 14/145,018

(22) Filed: Dec. 31, 2013

(65) Prior Publication Data
US 2015/0182176 A1    Jul. 2, 2015

(51) Int. Cl.
*A61B 6/00*        (2006.01)
*A61B 6/03*        (2006.01)

(52) U.S. Cl.
CPC .............. *A61B 6/4241* (2013.01); *A61B 6/032* (2013.01); *A61B 6/482* (2013.01)

(58) Field of Classification Search
CPC ........ A61B 6/032; A61B 6/035; A61B 6/482; A61B 6/4241
USPC ...................................................... 378/5, 901
See application file for complete search history.

(56) References Cited

U.S. PATENT DOCUMENTS

| | | | |
|---|---|---|---|
| 6,901,337 B2 | 5/2005 | Tanaka et al. | |
| 7,480,362 B2 | 1/2009 | Carmi | |
| 7,573,040 B2 | 8/2009 | Tkaczyk et al. | |
| 7,724,865 B2 | 5/2010 | Wu et al. | |
| 7,800,070 B2 | 9/2010 | Weinberg et al. | |
| 7,855,370 B2 | 12/2010 | Mott | |
| 7,894,576 B2 | 2/2011 | Carmi | |
| 8,055,039 B2 | 11/2011 | Wu et al. | |
| 8,315,352 B2 | 11/2012 | Wu et al. | |
| 2007/0076842 A1 | 4/2007 | Tkaczyk et al. | |
| 2009/0080597 A1 | 3/2009 | Basu | |
| 2011/0017918 A1 | 1/2011 | Baeumer et al. | |
| 2012/0039440 A1 | 2/2012 | Fan et al. | |

OTHER PUBLICATIONS

Taguchi et al., "An Analytical Model of the Effects of Pulse Pileup on the Energy Spectrum Recorded by Energy Resolved Photon Counting X-Ray Detectors", Medical Physics, pp. 3957-3969, vol. 37, Issue 8, 2010.

Wang et al., "Pulse Pileup Statistics for Energy Discriminating Photon Counting X-Ray Detectors", Medical physics, pp. 4265, vol. 38, Issue 7, 2011.

Ding et al., "Image-Based Spectral Distortion Correction for Photon-Counting X-Ray Detectors", Medical Physics, pp. 1864-1876, vol. 39, Issue 4, 2012.

*Primary Examiner* — Jurie Yun
(74) *Attorney, Agent, or Firm* — Fletcher Yoder, P.C.

(57) ABSTRACT

A system includes an energy-discriminating, photon-counting X-ray detector, comprising a plurality of detector cells adapted to produce projection data in response to X-ray photons and to produce an electrical signal having a recorded count for the energy bins and a total energy intensity. The system also includes data processing circuitry adapted to receive the electrical signal, to generate a simulated count rate for each of the energy bins by using the total energy intensity, to determine a set of energy intensity dependent material decomposition vectors, and, for the measured projection data, to perform material decomposition.

20 Claims, 4 Drawing Sheets

SYSTEMS AND METHODS FOR CORRECTING DETECTOR ERRORS IN COMPUTED TOMOGRAPHY IMAGING

BACKGROUND

The subject matter disclosed herein generally relates to medical imaging systems and methods. More particularly, the disclosed subject matter relates to systems and methods for correcting errors arising due to a pile-up effect with energy-discriminating, photon-counting detectors when performing material decomposition.

In modern medicine, medical professionals routinely desire to conduct patient imaging examinations to assess the internal condition of a patient in a non-invasive manner. For typical single-energy computed tomography (CT) imaging, the resulting X-ray images are largely a representation of the average density of each analyzed voxel based upon the patient's attenuation of X rays emitted by the X-ray source and detected by the X-ray detector. However, for multi-energy X-ray imaging, a greater amount of imaging data may be gleaned for each voxel, such as an estimate of the type of material in each analyzed voxel. For example, in a dual-energy X-ray imaging system, X-ray spectra with two different energy distributions are employed; higher-energy X-ray photons generally interact substantially less with patient tissue than the lower-energy X-rays. In order to reconstruct multi-energy CT projection data, the underlying physical effects of X-ray interaction with matter are considered, namely, the Compton scattering effects and photoelectric effects, in a process known as material decomposition (MD). Using these techniques, it is possible to identify two or more constituent components in each analyzed voxel.

During multi-energy CT projection data acquisition, a multi-energy X-ray source may be used to generate X-ray spectra having different energy distributions and may be capable of quickly switching from emitting a spectrum having a specific mean energy to emitting a spectrum having a different mean energy, by quickly modifying the peak operating voltage (kVp) of the X-ray tube. Once the X-ray source emits the X-ray spectrum containing a distribution of photon energies, these photons typically pass through a patient or object where they are partially attenuated before reaching an X-ray detector. Typically in such systems, an energy-integrating detector (the energy deposited by the X-ray photons impinging upon the detector cell during an integration period is summed) is used with an X-ray source that rapidly modulates the operating voltage of the X-ray tube. However, another approach for multi-energy imaging is to use an X-ray source emitting a single spectrum and an energy-integrating, photon-counting detector (the detector estimates the energy of each detected photon and tallies the number of photons detected in each of a finite number of energy bins during an integration interval).

An energy-discriminating, photon-counting detector is especially useful in multiple-energy X-ray applications due to this energy-discriminating capability. However, one obstacle impeding its clinical utility is the current count rate capability of this detector technology: the incident photon flux rate required for clinical CT imaging is beyond the counting capability of currently-available energy-discriminating, photon-counting detectors, thus giving rise to a pile-up effect that results in dramatic distortions in the detected signal. The pile-up effect occurs when detector sensor material and electronics cannot keep pace with the incident X-ray flux rate. The energy from multiple photons is deposited during a charge-integration interval in the detector; both the count and energy of detected photons are erroneous if the incident photon flux rate is too high. While methods have been proposed to use the amplitude profile of the detected spectrum to generate a correction for pile-up effect, such methods do not account for the need to perform material decomposition often used for multi-energy imaging. Accordingly, there exists a need for systems and methods that mitigate these limitations.

BRIEF DESCRIPTION

In one embodiment, a multi-energy computed tomography (CT) imaging system includes an energy-discriminating, photon-counting X-ray detector having at least two energy bins and being adapted to produce a projection data signal in response to X-ray photons that reach the X-ray detector. The detector is also adapted to produce a recorded photon count for each of the at least two energy bins during a data acquisition time period and a signal representing the total energy deposited during the data acquisition time period. Data processing circuitry is adapted to receive the electrical signal from the energy-discriminating, photon-counting X-ray detector, to generate a simulated count rate for each of the at least two energy bins by using the total energy signal in a detector pile-up model, to determine a set of energy intensity dependent material decomposition vectors, and, for each ray in the set of projection data measurements, to perform material decomposition by utilizing the simulated count rate for each of the at least two energy bins and a material decomposition vector selected from the set of energy intensity dependent material decomposition vectors and corresponding to the measured energy intensity of the ray.

In another embodiment, a method includes receiving a projection data signal generated by an energy-discriminating, photon-counting X-ray detector in response to X-ray photons that reached the X-ray detector during a data acquisition time period and receiving an electrical signal characterizing a total energy intensity recorded by the energy-discriminating, photon-counting X-ray detector during the data acquisition time period. The method also includes simulating a photon count rate for each of at least two energy bins by using the electrical signal characterizing the total energy intensity in a detector pile-up model and determining a set of energy intensity dependent material decomposition vectors. The method further includes performing, for each ray in the set of projection data measurements, material decomposition by utilizing the simulated photon count rate for each of the at least two energy bins and a material decomposition vector selected from the set of energy intensity dependent material decomposition vectors and corresponding to the measured energy intensity of the ray.

In another embodiment, a non-transitory computer readable medium encodes one or more executable routines, which, when executed by a processor, cause the processor to perform acts including receiving a projection data signal generated by an energy-discriminating, photon-counting X-ray detector in response to X-ray photons that reached the X-ray detector during a data acquisition time period and receiving an electrical signal characterizing the total energy intensity recorded by the energy-discriminating, photon-counting X-ray detector during the data acquisition time period. The acts also include simulating a photon count rate for each of at least two energy bins by using the electrical signal characterizing the total energy intensity in a detector pile-up model and determining a set of energy intensity dependent material decomposition vectors. The acts further include performing, for each ray in the set of projection data measurements, material decomposition by utilizing the simulated photon count rate for each of the at least two energy bins and a material decomposition vector selected from the set of energy intensity dependent material decomposition vectors and corresponding to the measured energy intensity of the ray.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

As described in more detail below, provided herein are systems and methods for combining detector pile-up correction and material decomposition in multi-energy X-ray imaging systems. Energy-discriminating, photon-counting detectors are widely recognized for their energy-discriminating capability, but their widespread clinical application has been impeded by the limited photon flux count rate capability that such detectors can accommodate. That is, the photon flux rate required to perform high-fidelity clinical computed tomography (CT) imaging exceeds the capabilities of the presently available energy-discriminating, photon-counting detectors. Even when the incident rate is a small fraction of the detector's maximum periodic count rate capability, a pile-up effect results in dramatic spectral distortions (both in terms of count and spectral shape) in the detected signal, thus presenting challenges for applying quantitative material decomposition methods as required in multi-energy CT imaging, denoted as spectral CT. For example, a detector pile-up effect occurs when the incident flux rate at the detector exceeds the maximum flux rate that the detector can accommodate. As a further example, in dual-energy embodiments, a detector pile-up effect may occur when the threshold count rates for the high- and low-energy bins are exceeded by the demands of the imaging operation.

In certain embodiments, the pile-up effects that result from use of energy-discriminating, photon-counting detector technology may lead to errors using material decomposition approaches that are known in the art, resulting in artifacts in the basis material density images that are generated through the material decomposition processing of the acquired projection data. Accordingly, the systems and methods disclosed herein include modeling of both the detector pile-up effect and the material decomposition process, thus reducing or eliminating the artifacts generated in the material density images and improving the material decomposition accuracy. Presently disclosed embodiments may offer distinct advantages over hardware-based solutions that attempt to increase the periodic rate of the detector by the several orders of magnitude that are required because the disclosed embodiments are more easily integrated into existing systems, thereby rendering such embodiments more cost effective. Further, the presently disclosed methods offer the benefit of computational efficiency, with certain embodiments having the same computational complexity as the projection-based material decomposition that are known in the art and used in currently-available, commercial, dual-energy CT products.

Figure 1:
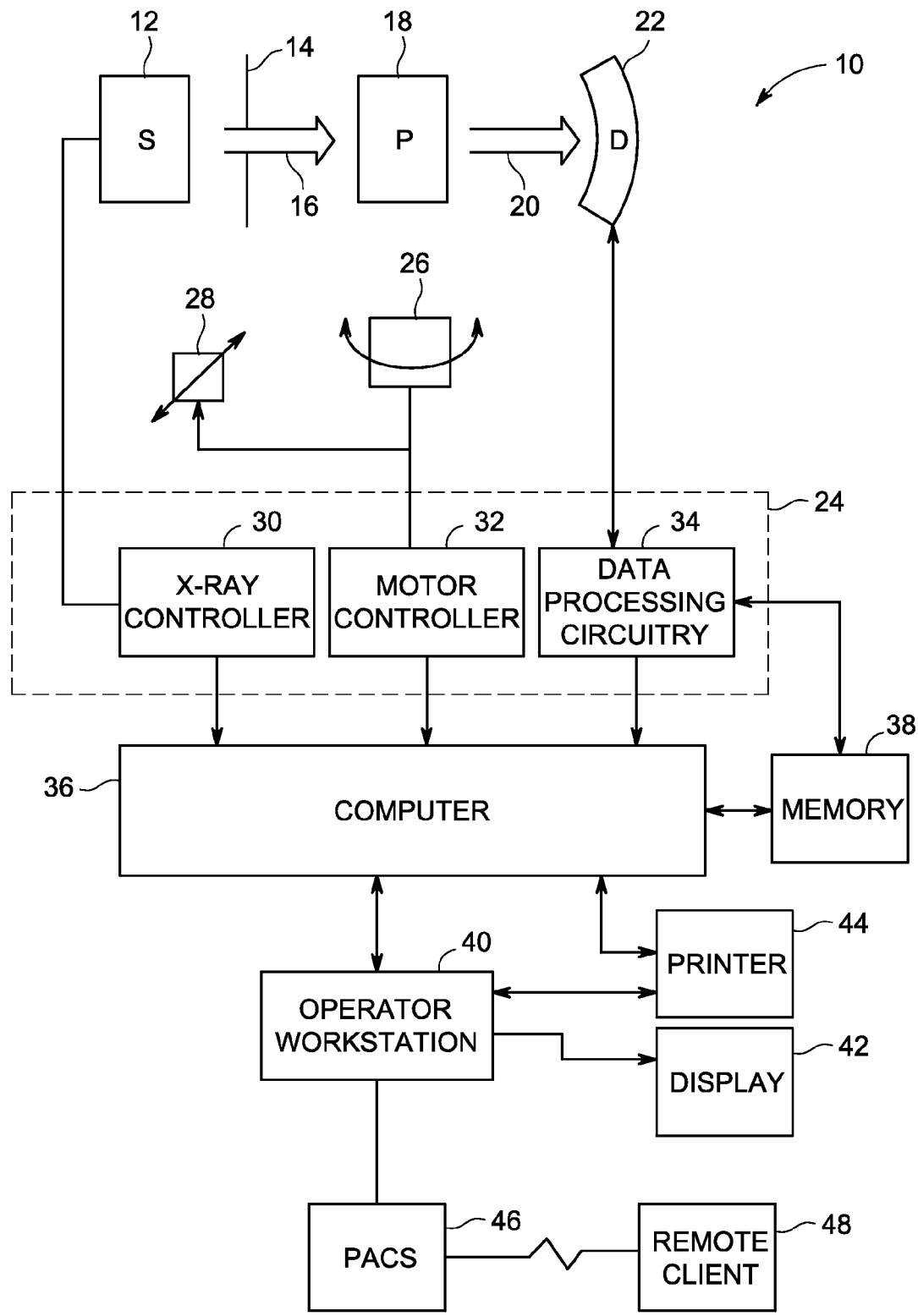
FIG. 1 illustrates an embodiment of a multi-energy CT imaging system in accordance with aspects of the present disclosure.

With the forgoing discussion in mind, FIG. 1 illustrates diagrammatically an imaging system 10 for acquiring and processing projection data. In the illustrated embodiment, system 10 is a multi-energy computed tomography (CT) system designed to acquire multi-energy and non-multi-energy X-ray projection data, to reconstruct the projection data into an image, and to process the image data for display and analysis in accordance with the present techniques. Though the imaging system 10 is discussed in the context of medical imaging, the techniques and configurations discussed herein are applicable in other non-invasive imaging contexts, such as baggage, part, or package screening. In the embodiment illustrated in FIG. 1, the multi-energy CT imaging system 10 includes a source 12 of X-ray radiation. As discussed in detail herein, the source 12 of X-ray radiation is a multi-energy X-ray source, such as an X-ray tube, or a distributed source configured to emit X-rays from different locations along a surface. For example, the multi-energy X-ray source 12 may include one or more addressable solid-state electron emitters. Such solid-state electron emitters may be configured as arrays of field emitters, including one-dimensional arrays, i.e., lines, and two-dimensional arrays. The multi-energy X-ray source is configured to emit X-rays of one or more stable energy spectra.

The multi-energy X-ray source 12 may be positioned proximate to a collimator 14. The collimator 14 may consist of one or more collimating regions, such as lead or tungsten shutters, for each emission point of the source 12. The collimator 14 typically defines the size and shape of the one or more beams of radiation 16 that pass through a region in which a subject, such as a human patient 18, is positioned. A beam of radiation 16 may be generally fan-shaped or cone-shaped, depending on the configuration of the detector array. An attenuated portion of the radiation 20 passes through the subject, which attenuates the X-ray beam, and impacts a detector array, represented generally at reference numeral 22.

The detector 22 is generally formed by a plurality of detector elements, which detect the X-rays that pass through and around a subject of interest. Each detector element produces an electrical signal that represents the intensity of the X-ray beam incident at the position of the element during the time the beam strikes the detector. Typically, signals are acquired at a variety of angular positions of an X-ray source 12 and detector 22 around the subject of interest 18 so that a plurality of radiographic views may be collected. These signals are acquired and processed to reconstruct a cross-sectional image of the features within the subject, as described below.

In certain embodiments, the detector 22 may be an energy-discriminating, photon-counting detector having at least two energy bins for the purpose of counting photons impinging on the detector within each of the energy bins. To that end, the detector 22 may include a plurality of individual detector cells coupled to a plurality of photon counters. In operation, the photons that impinge upon the detector cells of the detector 22 are counted by the photon counter and tallied in their corresponding energy bins. One or more electrical signals may be generated based on this recorded information. For example, an electrical signal encoding a count for each of the at least two energy bins during a data acquisition interval may be generated and transmitted to control or processing circuitry for further downstream processing, for example, to extract information about the material composition within the patient 18.

The multi-energy X-ray source 12 is controlled by a system controller 24, which furnishes power, focal spot location, control signals and so forth for CT examination sequences. Moreover, the detector 22 is coupled to the system controller 24, which commands acquisition of the signals generated in the detector 22. The system controller 24 may also execute various signal processing and filtration functions, such as for initial adjustment of dynamic ranges, interleaving of digital image data, and so forth. In general, system controller 24 commands operation of the imaging system to execute examination protocols and to process acquired projection data. In the present context, system controller 24 also includes signal processing circuitry and associated memory circuitry. The associated memory circuitry may store programs and routines executed by the system controller, configuration parameters, image data, and so forth. In one embodiment, the system controller 24 may be implemented as all or part of a processor-based system such as a general-purpose or application-specific computer system.

In the embodiment illustrated in FIG. 1, system controller 24 may control the movement of a linear positioning subsystem 28 and rotational subsystem 26 via a motor controller 32. In imaging systems 10 in which the source 12 and/or the detector 22 may be rotated, the rotational subsystem 26 may rotate the X-ray source 12, the collimator 14, and/or the detector 22 through one or multiple turns around the patient 18. It should be noted that the rotational subsystem 26 may include a gantry. The linear positioning subsystem 28 enables the patient 18, or more specifically a patient table, to be displaced linearly within a gantry. Thus, the patient table may be linearly moved within the gantry or within the imaging volume defined by source 12 and/or detector 22 configuration to generate images of particular areas of interest within the patient 18. In embodiments comprising a stationary source 12 and a stationary detector 22, the rotational subsystem 26 may be absent. Similarly, in embodiments in which the source 12 and the detector 22 are configured to provide extended or sufficient coverage along the Z-axis, i.e., the axis associated with the main length of the patient 18, the linear positioning subsystem 28 may be absent.

Further, the system controller 24 may include data processing circuitry 34. In this embodiment, the detector 22 is coupled to the system controller 24, and more particularly to the data processing circuitry 34. The data processing circuitry 34 receives data collected by the detector 22. In embodiments in which the detector 22 is an energy-discriminating, photon-counting detector, the energy-discriminating, photon-counting detector converts the input signal into photon counts and transmits the acquired data to the data processing circuitry 34. In certain embodiments, the data processing circuitry 34 may be selectively activated by the system controller 24 (e.g., via activation signals) to receive signals from the detector 22.

Additionally, the multi-energy X-ray source 12 may be controlled by an X-ray controller 30 disposed within the system controller 24. The X-ray controller 30 may be configured to provide power and timing signals to the X-ray source 12. For example, the X-ray controller 30 may include a fast-switching power supply configured to supply the source 12 with at least two or more stable biases to produce X-ray beams comprising two or more stable energy spectra.

In the depicted embodiment, the computer 36 is coupled to the system controller 24. The data collected by the data processing circuitry 34 may be transmitted to the computer 36 for subsequent processing and reconstruction. The computer 36 may include or communicate with a memory 38 that can store data processed by the computer 36, data to be processed by the computer 36, or routines to be executed by the computer 36, such as for processing image data in accordance with the present techniques. It should be understood that any type of computer accessible memory device capable of storing the desired amount of data and/or code may be utilized by such a system 10. Moreover, the memory 38 may include one or more memory devices, such as magnetic or optical devices, of similar or different types, which may be local and/or remote to the system 10. The memory 38 may store data, processing parameters, and/or computer programs having one or more routines for performing the processes described herein.

The computer 36 may also be adapted to control features enabled by the system controller 24, i.e., scanning operations and data acquisition. Furthermore, the computer 36 may be configured to receive commands and scanning parameters from an operator via an operator workstation 40 which may be equipped with a keyboard and/or other input devices. An operator may thereby control the system 10 via the operator workstation 40. Thus, the operator may observe the reconstructed image and other data relevant to the system from computer 36, initiate imaging, select and apply image filters, and so forth. Further, the operator may manually identify features and regions of interest from the reconstructed image or the operator may review features and regions of interest automatically identified and/or enhanced through computer-aided geometry determination as discussed herein. Alternatively, automated detection algorithms may be applied to such enhanced features or regions of interest.

A display 42 coupled to the operator workstation 40 may be utilized to observe the reconstructed image. Additionally, the reconstructed image may be printed by a printer 44 that may be coupled to the operator workstation 40. The display 42 and printer 44 may also be connected to the computer 36, either directly or via the operator workstation 40. Further, the operator workstation 40 may also be coupled to a picture archiving and communications system (PACS) 46. It should be noted that PACS 46 might be coupled to a remote system 48, radiology department information system (RIS), hospital information system (HIS) or to an internal or external network, so that others at different locations may gain access to the image data.

One or more operator workstations 40 may be linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

As discussed above, in certain embodiments, the detector 22 may be an energy-discriminating, photon-counting detector, and the incident photon flux of the protocol required for a clinical CT imaging operation may exceed the detection capabilities of the energy-discriminating, photon-counting detector, thus resulting in a detector pile-up effect in the measured data. Accordingly, embodiments of methods for correcting for the pile-up effect and performing an integrated material decomposition process are provided in FIGS. 2 and 3 and shown schematically in FIGS. 4 and 5.

For X-ray CT applications utilizing an energy-discriminating, photon-counting detector with two energy bins, the detected photon intensity in low- and high-energy bins, $S_1$ and $S_2$ respectively—assuming full absorption in the detector—can be written as:

$$S_1 = \int S_{01}(E)\exp\left[-\left(\frac{\mu}{\rho}\right)_1(E)\cdot\delta_1 - \left(\frac{\mu}{\rho}\right)_2(E)\cdot\delta_2\right]dE \quad (2.1)$$

$$S_2 = \int S_{02}(E)\exp\left[-\left(\frac{\mu}{\rho}\right)_1(E)\cdot\delta_1 - \left(\frac{\mu}{\rho}\right)_2(E)\cdot\delta_2\right]dE \quad (2.2)$$

where $S_{01}(E)$ and $S_{02}(E)$ are the count rate in the low- and high-energy bins, respectively, of air scan (scan with no object in the X-ray beam), $$\left(\frac{\mu}{\rho}\right)_1(E) \text{ and } \left(\frac{\mu}{\rho}\right)_2(E)$$

are the mass attenuation coefficients of the two basis materials as a function of energy, $\delta_1$ and $\delta_2$ are the line integral of the density distribution of basis materials (denoted as area density), which are independent of energy, given by:

$$\delta_1 = \int \rho_1(\vec{r})dl \quad (2.3)$$

$$\delta_2 = \int \rho_2(\vec{r})dl \quad (2.4)$$

Although not specifically denote in the above equation, this process occurs for each detector cell in detector 22.

Note that the energy-discriminating, photon-counting detector can record not only the count in each energy bin, but also the integral of the total energy intensity deposited in the detector for all photon interaction events occurring within a dead-time period (a period when the detector is estimating the energy level of the photon). Thus, the deposited energy intensity is accurate even in the case of severe pile-up at high photon flux rates. This total energy intensity can be written as:

$$I = \int S_0(E)\cdot E \cdot \exp\left[-\left(\frac{\mu}{\rho}\right)_1(E)\cdot\delta_1 - \left(\frac{\mu}{\rho}\right)_2(E)\cdot\delta_2\right]dE \quad (2.5)$$

where $S_0(E)$ is the count rate of air scan, and the detected photon flux at each energy level is weighted by the energy level E.

The goal of the material decomposition process is to calculate $(\delta_1, \delta_2)$ from the measurements $(S_1, S_2)$. In the presently disclosed embodiments, a 2D polynomial fitting is used to generate the decomposition vectors, i.e.

$$\delta_1 = \Sigma_{i,j}\alpha_{ij}^{(1)}S_{1,N}^i S_{2,N}^j \quad (2.6)$$

$$\delta_2 = \Sigma_{i,j}\alpha_{ij}^{(2)}S_{1,N}^i S_{2,N}^j \quad (2.7)$$

Where the i j terms of $\alpha^{(1)}$ and $\alpha^{(2)}$ collectively are decomposition vectors for $\delta_1$ and $\delta_2$, respectively. For example, in certain embodiments for medical imaging, the decomposition vectors may correspond to two chosen basis materials typical of materials within the human body (e.g., water and iodine, for contrast-enhanced CT examinations). $S_{1,N}$ and $S_{2,N}$ are the count rates in the low- and high-energy bins normalized to that of the air scan:

$$S_{1,N} = \frac{S_1}{\int S_{01}(E)dE} \quad (2.8)$$

$$S_{2,N} = \frac{S_2}{\int S_{02}(E)dE} \quad (2.9)$$

In the ideal case, equations (2.1) and (2.2) give the model of material decomposition, which is independent of the total energy intensity deposited in the detector cell, as computed in (2.5). However, in the case of high incident photon flux rate with the detector pile-up effect, the detected spectra are distorted and the total energy intensity I needs to be taken into consideration.

Figure 2:
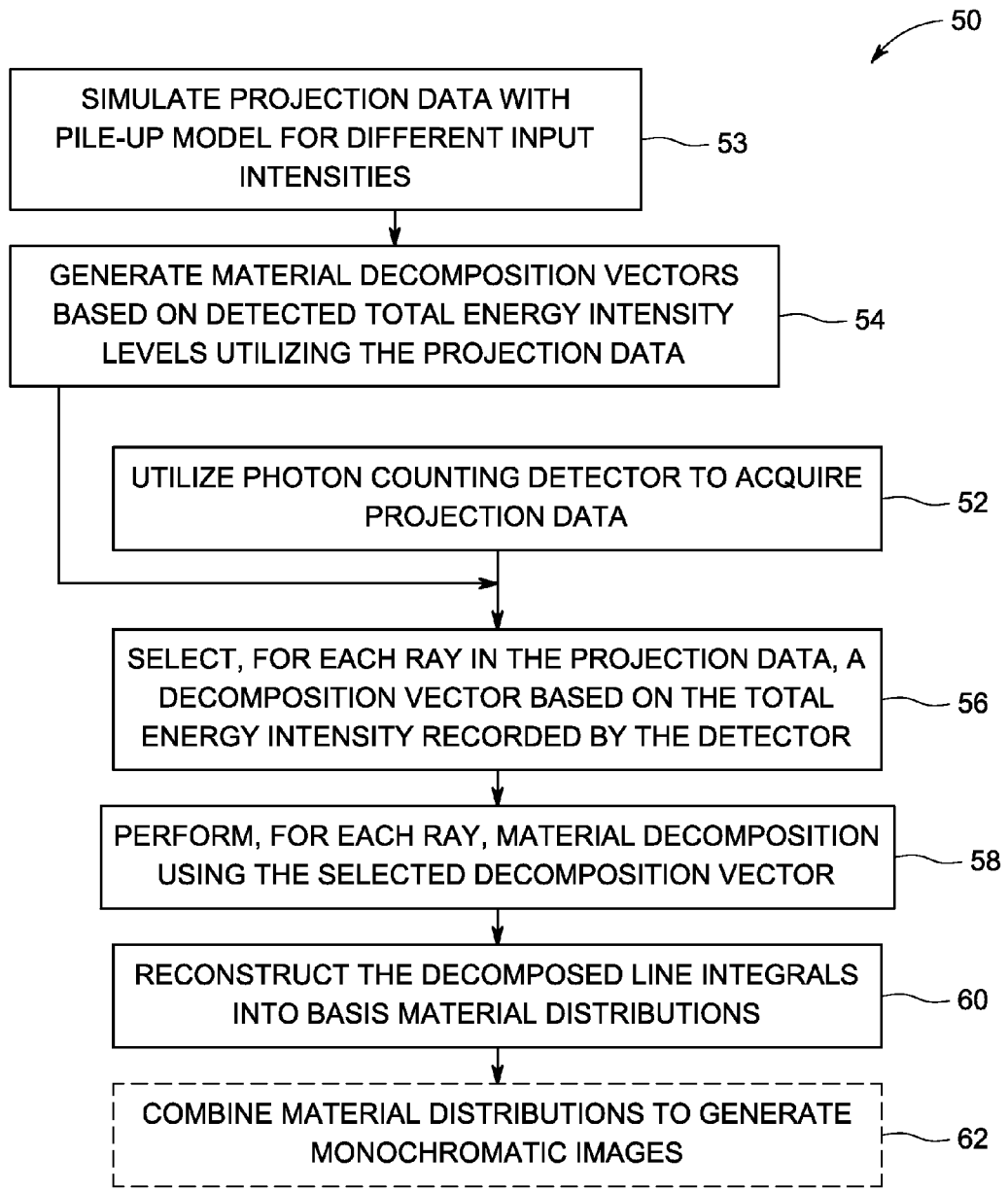
FIG. 2 illustrates an embodiment of a method of performing detector pile-up correction and material decomposition for energy intensities having discrete values.

For instances of discrete energy intensities, the material decomposition and pile-up correction can be implemented in the steps set forth in the method 50 of FIG. 2. Specifically, the energy-discriminating, photon-counting detector is utilized to acquire the projection data (block 52). The projection data is simulated with the detector pile-up model for different input intensities (block 53) using various area densities of basis materials (the product of basis material density and various ray path lengths); the material decomposition vectors for the chosen material basis pair (e.g., water and iodine) are generated based on the detected total energy intensities (block 54). For each input energy intensity level, the acquired projection data (i.e., the count rate in the multiple energy bins) are simulated based on a detector pile-up model, and the decomposition vectors are generated considering the measured projection data with or without normalization to the air scan.

For example, in one embodiment, the material decomposition vectors may be generated with a two-dimensional (2D) polynomial fitting at a set of different input energy intensity levels. For each input energy intensity level, the count rate in the low energy bin and the count rate in the high energy bin can be simulated based on equation (2.1) and equation (2.2), selected values for area densities for the basis materials as computed in equations (2.3) and (2.4), and a detector pulse pile-up model. It should be noted that the embodiments disclosed herein are compatible with any model that models the detector pile-up that occurs in an energy-discriminating, photon-counting detector when the photon flux exceeds the detection capabilities of the detector. However, in one embodiment, the pulse pile-up model utilizes techniques disclosed in the following reference, which is hereby incorporated in its entirety into the present disclosure for all purposes—: Wang, Adam S., et al. "Pulse pileup statistics for energy discriminating photon counting X-ray detectors." *Medical Physics* 38 (2011): 4265. For a set of total energy intensity levels, the corresponding material decomposition vectors can be denoted as $\alpha(I^{(1)})$, $\alpha(I^{(2)})$, $\alpha(I^{(N)})$. The simulated count rate in the low-energy and high-energy bins using the detector pile-up model can be scaled by the data acquisition interval to generate a specific count in each energy bin that corresponds to measurements acquired with an energy-discrimination, photon-counting detector.

In the illustrated embodiment, the method 50 proceeds with selection of the proper decomposition vector based on the total energy intensity recorded by the detector for each ray in the projection data (block 56). For example, for each ray in the projection data, the proper decomposition vector $\alpha^{(1)}$ and $\alpha^{(2)}$ is determined using a predefined rule:

$$\alpha_{ij}^{(1)}(I) = \alpha_{ij}^{(1)}(I^{(n-1)}), \text{ for } I\in [I^{(n-1)}, I^{(n)}) \quad (2.10)$$

$$\alpha_{ij}^{(2)}(I) = \alpha_{ij}^{(2)}(I^{(n-1)}), \text{ for } I\in [I^{(n-1)}, I^{(n)}) \quad (2.10)$$

where $I^{(n)}$ (n=1, 2, ..., N) is a set of total energy intensity levels that increases monotonically, and $\alpha(I^{(n)})$ is the corresponding material decomposition vectors at the discrete total energy intensity levels. Although not shown, one could consider nearest neighbor interpolation, where the decomposition vector $\alpha^{(1)}$ and $\alpha^{(2)}$ are chosen by considering the simulated $I^{(n-1)}$ value that is less than the total energy intensity measurement and the simulated $I^{(n)}$ value that is greater than the total energy intensity measurement. The decomposition vectors $\alpha^{(1)}$ and $\alpha^{(2)}$ are then chosen by considering the absolute difference between the measured total energy intensity value and the simulated $I^{(n-1)}$ and $I^{(n)}$ values that bracket the measurement, and selecting the decomposition vectors corresponding to the simulated value that has the minimum absolute difference from the measurement.

The selected decomposition vectors are then utilized to perform material decomposition for each ray in the acquired projection data (block 58). For example, for each ray, the material decomposition may be performed using the calculated vector and equations (2.6) and (2.7). Further, in certain embodiments, normalization of the projection data is performed in accordance with the generation of the decomposition vector in block 54. After decomposing the projection data into the line integrals of the density of the basis materials, the line integrals are reconstructed into basis material cross-sectional distributions (block 60). If desired, the cross-sectional material distributions may be combined to generate monochromatic images (block 62).

Figure 3:
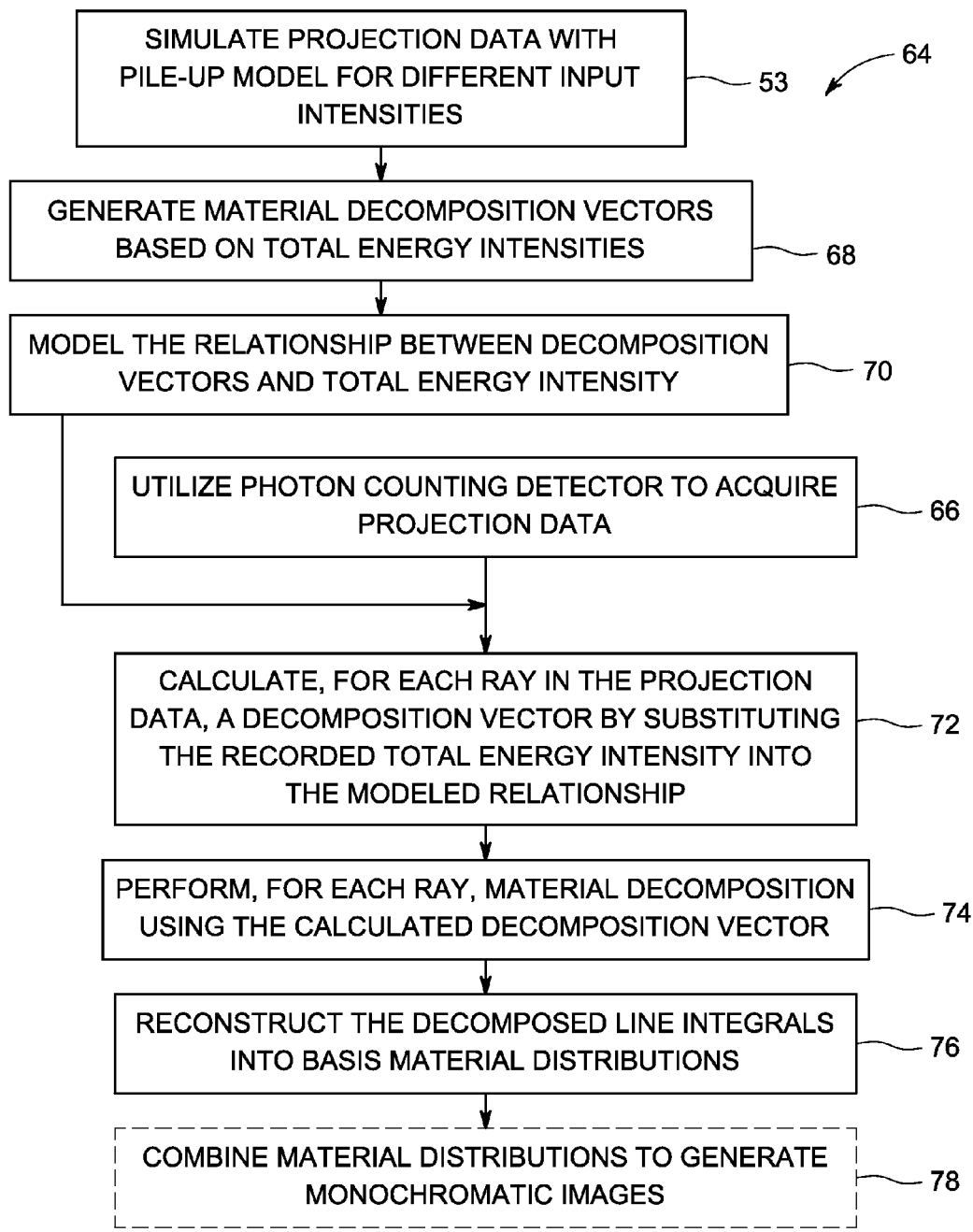
FIG. 3 is a diagram illustrating calculation of a set of energy intensity dependent decomposition vectors in accordance with a presently disclosed embodiment.

FIG. 3 illustrates a further embodiment of the method 50 illustrated in FIG. 2. In this embodiment, an additional model is used for the relationship between the decomposition vector and total energy intensity, thus enabling the total energy intensity to have a continuous value, rather than a discrete value, as in the embodiment of FIG. 2. Specifically, the method 64 includes the step of utilizing the energy-discriminating, photon-counting detector to acquire the projection data (block 66). The projection data is simulated with the pile-up model for different input intensities (block 53) and material decomposition vectors are generated based on the total energy intensities (block 68). Here again, for each input energy intensity level, the projection data are simulated based on a detector pile-up model. However, in this embodiment, the relationship between the decomposition vectors and the total energy intensity levels is modeled (block 70), thus enabling the energy intensities to have continuous rather than discrete values. This step is shown in more detail below in the schematics of FIGS. 4 and 5.

For each ray in the acquired projection data, the proper decomposition vector is calculated by substituting the total energy intensity recorded by the detector into the model generated in block 72. The calculated vectors are then used to perform material decomposition for each ray (block 74). After decomposing the projection data into line integrals of the density of selected basis materials, the line integrals are reconstructed into basis material cross-sectional distributions (block 76). If desired, the cross-sectional material distributions may be combined to generate monochromatic images (block 78).

Figure 4:
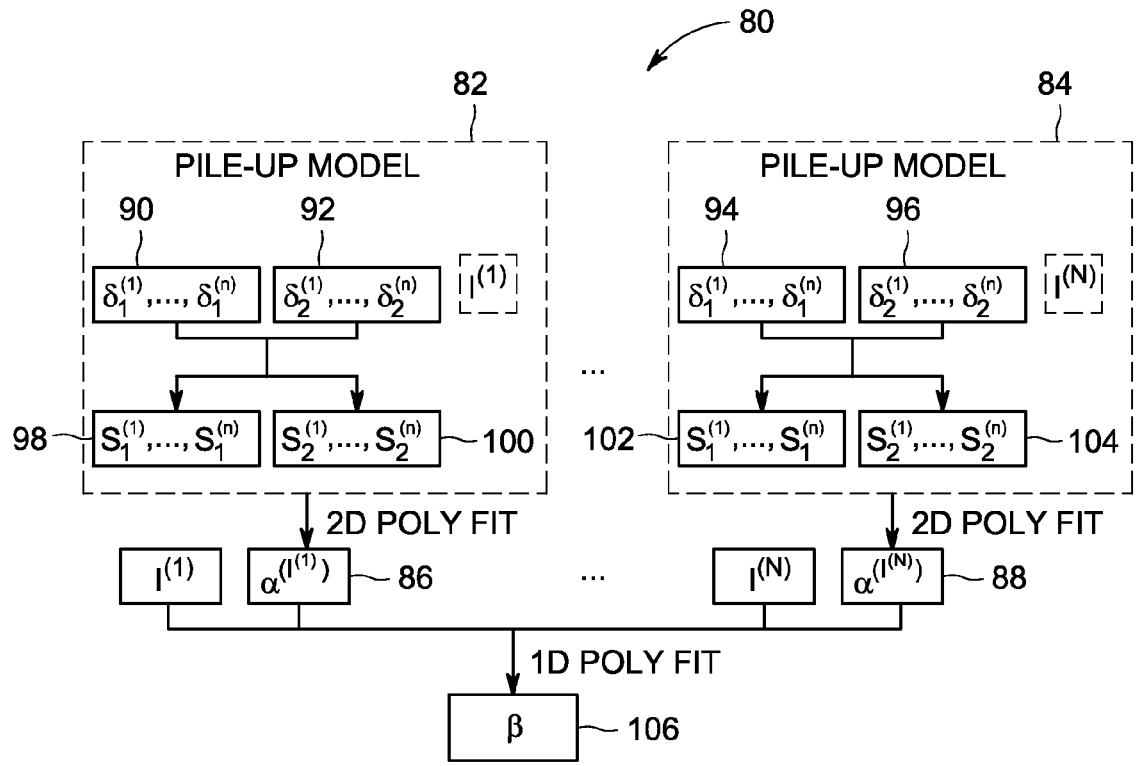
FIG. 4 is a diagram illustrating a material decomposition process in accordance with a presently disclosed embodiment.
Figure 5:
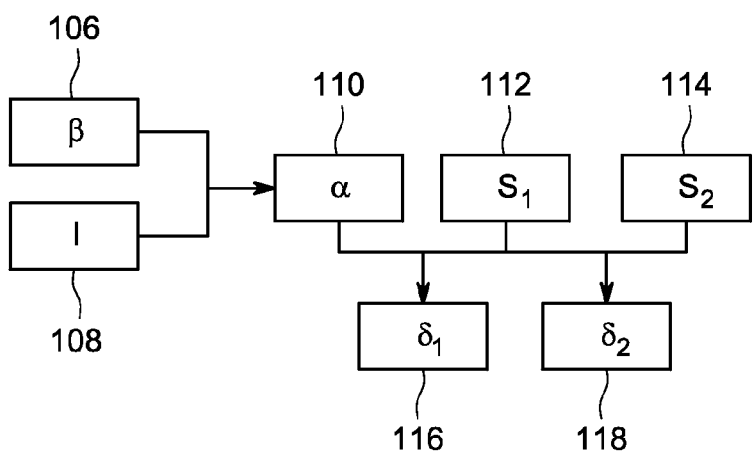
FIG. 5 illustrates an embodiment of a method of performing detector pile-up correction and material decomposition for energy intensities having continuous values.

FIGS. 4 and 5 schematically illustrate the steps of the combined pile-up correction and material decomposition methods 50 and 64. More specifically, FIG. 4 illustrates an embodiment of a calculation of a total energy intensity dependent decomposition vector ($\beta$). FIG. 5 illustrates an embodiment of the material decomposition process utilizing the measured count, the decomposition vector, and the total energy intensity.

In the schematic 80 of FIG. 4, blocks 82 and 84 illustrate generation of a set of decomposition vectors 86 and 88 for each of the rays in the set of simulated projection data. As shown, the line integral of the density distribution of the selected basis materials 90, 92, 94, and 96 are used in an attenuation model (e.g., as given by equations (2.1) and (2.2)) to provide input to the detector pile-up model, thus enabling generation of simulated values for the detected counts in the low- and high-energy bins 98, 100, 102, and 104 for a given integration interval. Once the simulated detected counts in each of the low- and high-energy bins are generated in this manner, a 2D polynomial fitting (e.g., as set forth in equations (2.6) and (2.7)) is used to generate the set of material decomposition vectors 86 and 88, each corresponding to total energy intensity in the acquired projection data. A one-dimensional (1D) polynomial fitting is then performed to generate $\beta$, the total energy intensity dependent decomposition vector shown in block 106. Mathematically the 1D polynomial fitting can be written as:

$$\alpha_{ij}^{(1)} = \Sigma_k \beta_{ij,k}^{(1)} \cdot I^k \qquad (2.12)$$

$$\alpha_{ij}^{(2)} = \Sigma_k \beta_{ij,k}^{(2)} \cdot I^k \qquad (2.13)$$

where $\alpha$ and I denote material decomposition vectors and the total energy intensity, respectively. FIG. 5 illustrates how $\beta$ 106 can be utilized in combination with the total energy intensity 108 detected by the detector to perform material decomposition. That is, since the total energy intensities detected by the energy-discriminating, photon-counting detector are within the capabilities of the detector even when the photon flux rate is not (e.g., in clinical CT applications), such intensities may be utilized to perform material decomposition even when the detected counts in the low- and high-energy bins for a specified integration internal are corrupted due to detector pile-up. As shown, the $\beta$ generated via the process illustrated in FIG. 4 is then utilized along with the detected total energy intensity in equations (2.12) and (2.13) to calculate the proper decomposition vectors 110. These calculated material decomposition vectors 110 are then utilized along with the measured high- and low-count values 112 and 114 to perform material decomposition in accordance with equations (2.6) and (2.7), thus generating the decomposed line integrals 116 and 118.

In this way, the pile-up correction and material decomposition may be combined into a single process. Further, the combined methods disclosed herein may be particularly advantageous when use of an energy-discriminating, photon-counting detector is desired, but the incident photon flux rate required for the clinical operation exceeds the capability of the detector. The provided methods may offer the benefits of reducing or eliminating the artifacts that would be generated in the material density images with a pile-up correction and improving the material decomposition accuracy.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. For example, these methods were described in the context of detector pile-up correction and material decomposition of measured projection data for CT imaging. However, these principles are equally applicable to X-ray imaging applications where projection images only are utilized.

The invention claimed is:

1. A multi-energy computed tomography (CT) imaging system comprising:
an energy-discriminating, photon-counting X-ray detector, comprising a plurality of detector cells each providing measurements corresponding to at least two energy bins and being configured to produce projection data in response to X-ray photons that reach the X-ray detector and to produce an electrical signal comprising a recorded count for each of the at least two energy bins recorded during a data acquisition time period and a total energy intensity recorded during the data acquisition time period; and
data processing circuitry configured to receive the electrical signal from one or more of the plurality of detector cells, to generate a simulated count rate for each of the at least two energy bins by using the total energy intensity in a detector pile-up model, to determine a set of energy intensity dependent material decomposition vectors, and, for each projection data measured by the one or more detector cells, to perform material decomposition by utilizing the measured count during a data acquisition time period for each of the at least two energy bins and a material decomposition vector selected from the set of energy intensity dependent material decomposition vectors and corresponding to the measured total energy intensity for the one or more of the plurality of detector cells.

2. The system of claim 1, comprising an X-ray source configured to emit X-rays in a direction toward the energy-discriminating, photon-counting X-ray detector.

3. The system of claim 2, comprising a subject positioned between the X-ray source and the energy-discriminating, photon-counting X-ray detector, wherein the X-ray photons that reach the energy-discriminating, photon-counting X-ray detector correspond to X-rays emitted by the X-ray source and attenuated by the subject.

4. The system of claim 1, wherein the data processing circuitry is configured to reconstruct decomposed projection data obtained via material decomposition into basis material cross-sectional distributions.

5. The system of claim 4, wherein the data processing circuitry is configured to combine the basis material cross-sectional distributions to generate one or more monochromatic images.

6. The system of claim 1, wherein an experimental photon flux rate during the data acquisition time period is greater than the count rate capability for the at least two energy bins.

7. The system of claim 1, wherein the data processing circuitry is configured to determine the set of energy intensity dependent material decomposition vectors by performing a two-dimensional polynomial fitting.

8. The system of claim 1, wherein the data processing circuitry is configured to model the relationship between the material decomposition vectors and the total energy intensity measured by one or more of the plurality of detector cells with a one-dimensional polynomial fitting.

9. A method, comprising:
receiving projection data generated by an energy-discriminating, photon-counting X-ray detector comprising a plurality of detector cells in response to X-ray photons that reached the X-ray detector during a data acquisition time period;
receiving an electrical signal comprising a total energy intensity recorded by one or more of the plurality of detector cells during the data acquisition time period;
simulating a photon count rate for each of at least two energy bins by using the total energy intensity contained in the electrical signal in a detector pile-up model;
determining a set of energy intensity dependent material decomposition vectors; and
performing, for projection data measured by the one or more of the plurality of detector cells, material decomposition by modeling the simulated photon count rate for each of the at least two energy bins and utilizing a material decomposition vector selected from the set of energy intensity dependent material decomposition vectors and corresponding to the measured total energy intensity for the one or more of the plurality of detector cells.

10. The method of claim 9, comprising reconstructing decomposed projection data obtained via the material decomposition into basis material cross-sectional distributions.

11. The method of claim 10, comprising combining the basis material cross-sectional distributions to generate one or more monochromatic images.

12. The method of claim 9, comprising receiving data corresponding to a measured count for each of the at least two energy bins recorded during the data acquisition time period.

13. The method of claim 9, wherein determining the set of energy intensity dependent material decomposition vectors comprises performing a two-dimensional polynomial fitting.

14. The method of claim 9, comprising modeling the relationship between the material decomposition vectors and the total energy intensity measured by one or more of the plurality of detector cells with a one-dimensional polynomial fitting.

15. A non-transitory computer readable medium encoding one or more executable routines, which, when executed by a processor, cause the processor to perform acts comprising:
receiving projection data generated by an energy-discriminating, photon-counting X-ray detector comprising a plurality of detectors cells providing measurements in response to X-ray photons that reached the X-ray detector during a data acquisition time period;
receiving an electrical signal comprising a total energy intensity recorded by one or more of the plurality of detector cells during the data acquisition time period;
simulating a photon count rate for each of at least two energy bins by using the total energy intensity contained in the electrical signal in a detector pile-up model;
determining a set of energy intensity dependent material decomposition vectors; and
performing, for each projection data measured by the one or more of the plurality of detector cells, material decomposition by modeling the simulated photon count rate for each of the at least two energy bins and utilizing a material decomposition vector selected from the set of energy intensity dependent material decomposition vectors and corresponding to the measured total energy intensity for the one or more of the plurality of detector cells.

16. The non-transitory computer-readable medium of claim 15, wherein the one or more routines, when executed by the processor, cause further acts to be performed comprising reconstructing decomposed projection data obtained via the material decomposition into basis material cross-sectional distributions.

17. The non-transitory computer-readable medium of claim 16, wherein the one or more routines, when executed by the processor, cause further acts to be performed comprising combining the basis material cross-sectional distributions to generate one or more monochromatic images.

18. The non-transitory computer-readable medium of claim 15, wherein the one or more routines, when executed by the processor, cause further acts to be performed comprising receiving data corresponding to a measured count for each of the at least two energy bins recorded during the data acquisition time period.

19. The non-transitory computer-readable medium of claim 15, wherein the one or more routines, when executed by the processor, cause further acts to be performed comprising modeling the relationship between the material decomposition vectors and the total energy intensity measured by the one or more of the plurality of detector cells with a one-dimensional polynomial fitting.

20. The non-transitory computer-readable medium of claim 15, wherein determining the set of energy intensity dependent material decomposition vectors comprises performing a two-dimensional polynomial fitting.

* * * * *